(12) United States Patent
Mandica et al.

(10) Patent No.: US 10,974,044 B2
(45) Date of Patent: Apr. 13, 2021

(54) DEVICE FOR APPLYING A PRODUCT TO BE DISTRIBUTED ON THE SKIN OF A USER BY IONTOPHORESIS AND COMPRISING MEANS FOR MEASURING THE ABSENCE OF PRODUCT AND CORRESPONDING PROCESS

(71) Applicant: SEB S.A., Ecully (FR)

(72) Inventors: Franck Mandica, Francheville (FR); Johan Sabattier, Mornant (FR)

(73) Assignee: SEB S.A., Ecully (FR)

( * ) Notice: Subject to any disclaimer, the term of this patent is extended or adjusted under 35 U.S.C. 154(b) by 133 days.

(21) Appl. No.: 15/773,941

(22) PCT Filed: Nov. 4, 2016

(86) PCT No.: PCT/FR2016/052869
§ 371 (c)(1),
(2) Date: May 4, 2018

(87) PCT Pub. No.: WO2017/077256
PCT Pub. Date: May 11, 2017

(65) Prior Publication Data
US 2018/0326207 A1 Nov. 15, 2018

(30) Foreign Application Priority Data
Nov. 6, 2015 (FR) ...................................... 1560680

(51) Int. Cl.
*A61N 1/30* (2006.01)
*A61N 1/32* (2006.01)
*A61M 35/00* (2006.01)

(52) U.S. Cl.
CPC .............. *A61N 1/30* (2013.01); *A61N 1/325* (2013.01); *A61M 35/00* (2013.01)

(58) Field of Classification Search
CPC .......... A61N 1/30; A61N 1/325; A61M 35/00
See application file for complete search history.

(56) References Cited

U.S. PATENT DOCUMENTS 3,662,176 A * 5/1972 Kamentsky ........... G06M 1/101
250/565
2002/0161323 A1 10/2002 Miller et al.
(Continued)

FOREIGN PATENT DOCUMENTS

| EP | 0 942 278 A2 | 9/1999 |
| FR | 2 980 370 A1 | 3/2013 |

(Continued)

OTHER PUBLICATIONS

International Search Report as issued in International Patent Application No. PCT/FR2016/052869, dated Feb. 3, 2017.

*Primary Examiner* — Amber R Stiles
(74) *Attorney, Agent, or Firm* — Pillsbury Winthrop Shaw Pittman LLP (57) ABSTRACT

A device for applying a product to be dispensed on a skin of a user by iontophoresis, includes: at least one storage container for storing the product to be dispensed; at least one dispensing cavity able to receive the product to be dispensed; at least one first iontophoresis electrode; an electronic control circuit; and a measuring system for measuring a physical or physico-chemical parameter, the measuring system being connected to the electronic control circuit and configured to send a signal indicative of a parameter measurement. The first iontophoresis electrode and the measuring system are installed in the dispensing cavity, the electronic control circuit being configured to compare the value of the physical or physico-chemical parameter measured in the cavity to a reference threshold value so as to detect if the product is absent from the cavity.

14 Claims, 5 Drawing Sheets

(56) References Cited

U.S. PATENT DOCUMENTS

2007/0277816 A1* 12/2007 Morrison .......... A61M 15/0085
128/200.16
2008/0262581 A1* 10/2008 Barsness ................ A61N 1/044
607/115

FOREIGN PATENT DOCUMENTS

| WO | WO 02/085451 A2 | 10/2002 | |
|----|----|----|----|
| WO | WO-02085451 A2 * | 10/2002 | ............... A61N 1/30 |
| WO | WO 2013/118114 A1 | 8/2013 | |

* cited by examiner

DEVICE FOR APPLYING A PRODUCT TO BE DISTRIBUTED ON THE SKIN OF A USER BY IONTOPHORESIS AND COMPRISING MEANS FOR MEASURING THE ABSENCE OF PRODUCT AND CORRESPONDING PROCESS

CROSS-REFERENCE TO RELATED APPLICATIONS

This application is the U.S. National Stage of PCT/FR2016/052869, filed Nov. 4, 2016, which in turn claims priority to French patent application number 1560680 filed Nov. 6, 2015. The content of these applications are incorporated herein by reference in their entireties.

1. FIELD OF THE INVENTION

This invention concerns the field of devices permitting the application of a cosmetic or therapeutic product to be distributed on the skin of a user. In particular, it deals with devices using the principle of iontophoresis to improve the delivery of a product's active ingredient through the different skin layers.

2. PRIOR ART

We know of a device for applying a product to be distributed on the skin by iontophoresis intended to improve the delivery of a product's active ingredient through the skin. From the document WO 2013/118114 we know of such a device which comprises a reservoir for the product to be applied, at least one first electrode able to generate an electric field so as to permit an active ingredient of the product to penetrate the skin, an electronic control circuit, and measuring means connected to the control circuit. These measuring means are able to measure parameters of the skin or the substance, of the quantity of product remaining in the reservoir or of the time elapsed in order to generate automatic distribution of product on the skin.

One of the problems connected to this device for applying product to be distributed is that this is a complex system involving all types of measuring means. The measurements taken at the skin are not precise, because the skin reacts differently from one user to another. For example, concerning an impedance measurement, the skin impedance varies especially according to the skin's hydration. In addition, a time delay circuit does not permit precise management of the product to be distributed and of the consumption of the latter. Finally, there is no instruction on the way to manage these various parameters for product distribution.

3. OBJECTIVES OF THE INVENTION

In particular, the invention aims to remedy all or a portion of the drawbacks of the prior art.

One objective of the invention is to provide a device for applying a product to be distributed by iontophoresis that makes it possible to know when there is no product so that the treatment is not interrupted, protecting the user's skin.

4. SUMMARY OF THE INVENTION

These objectives are achieved through a device for applying a product to be distributed on the skin of a user by iontophoresis and comprising:

at least one means for storing the product to be distributed;
at least one distribution cavity able to receive the product to be distributed;
at least one first electrode for iontophoresis;
an electronic control circuit;
means for measuring a physical or physicochemical parameter connected to the electronic control circuit and configured to send a signal indicating the parameter measurement, the first electrode for iontophoresis and the measuring means are installed in the distribution cavity, the electronic control circuit being configured to compare the measured value of the physical or physicochemical parameter in the cavity with a threshold reference value so as to detect an absence of product in the cavity.

This solution permits solving the aforementioned problems. Therefore, the product application device permits having information at all times on the absence of product in the distribution cavity and thus on the user's skin. The device or the user having knowledge of this information triggers distribution of the product toward the user's skin. Knowing that there is no more product in the distribution cavity avoids microlesions occurring during prolonged application of current and/or friction of the device on the skin without the product, and thus without possible treatment. Also, the means for measuring a physical or physicochemical parameter in the distribution cavity permits a more precise measurement than measurements performed directly on the user's skin.

According to a characteristic of the invention, the device comprises at least one second electrode for iontophoresis arranged in the distribution cavity. Thus, the circulation of current remains located between the first electrode and the second electrode in the zone to be treated, while in a device described as monopolar, the current crosses a large part of the body (for example, hand, face and brain if a counter electrode is on the body of the device in contact with the palm of the hand).

According to a characteristic of the invention, the electronic control circuit is configured, if it detects the absence of product in the distribution cavity, to generate a command signal able to trigger distribution of product in the distribution cavity. As such, the product is distributed automatically, and the user may continue to treat the different zones of the skin without worrying about other controls of the device.

According to yet another characteristic of the invention, the electronic control circuit is connected to the first and second electrodes for iontophoresis and is configured to generate an electric current able to circulate on the skin side between the first and second electrodes for iontophoresis. Thus, it is possible to manage the circulation of current in the iontophoresis electrodes in order, on the one hand, not to disturb the measuring means, and on the other hand, to manage the application device's consumption of energy/electricity.

According to another characteristic of the invention, the device comprises alert means connected to the electronic control circuit, the electronic control circuit being configured, if it detects the absence of product in the distribution cavity, to generate a command signal able to alert the user to the absence of product in the cavity. The user is thus alerted to the absence of product in the cavity and can decide himself whether to continue the treatment or care of the skin treatment zones.

According to another characteristic of the invention, the device comprises at least one means for extracting the product to be distributed from the storage means. In particular, this extraction means may be operated manually or by motor. Thus, when the user is alerted to the lack of product, he can activate the extraction means in order to extract the product from the storage means otherwise, the extraction of product from the storage means is automated.

According to a first embodiment of the invention, the measuring means comprise a means of measuring the impedance of the product. Such a means of measuring impedance permits associating a detection threshold with the type of product to be distributed, which may be more or less conductive depending on its composition.

According to a characteristic of this embodiment, the impedance measuring means comprises at least one pair of electrodes for the measurement of impedance, which are arranged in the distribution cavity and between which an electric current circulates.

According to a second embodiment of the invention, the measuring means comprise an optical measuring means. Such an optical measuring means permits, in particular, avoiding problems with oxidation of the measurement electrodes described in the preceding embodiment if they are used in contact with oxidizing or corrosive products, for example.

According to a characteristic of this second embodiment, the optical measuring means comprises at least one light transmitter diffusing a light through at least one of the distribution cavities and at least one light receiver placed opposite the transmitter.

According to a characteristic of the invention, the first and the second electrodes for iontophoresis are separated by an inter-electrode zone which comprises a surface of application of the product on the skin. As such, the first and second electrodes for iontophoresis are kept at a distance from each other. In addition, this permits generating a current of lower intensity in these electrodes for safety measures.

According to yet another characteristic of the invention, the first and second electrodes for iontophoresis are situated in the same plane. This configuration permits reducing the distance traveled by the electric current between the first and second electrodes for iontophoresis compared to a device comprising one electrode for iontophoresis able to be in contact with the treatment or care zone and a second electrode for iontophoresis on a handle of the device. In addition, the penetration of the active ingredients through the user's skin is controlled. As such, it is possible to target the skin zone to be treated and limit the leakage currents.

According to a characteristic of the invention, the application surface is situated in a plane parallel to the said plane of the first and second electrodes, the plane of the first and second electrodes for iontophoresis and the plane of the inter-electrode zone being situated at a predetermined distance. In this way, arranging the first and second electrodes set back from the inter-electrode zone avoids direct contact of the electrodes with the user's skin, which prevents irritation or electrical tingling. This also permits reducing the quantity of product that can remain/accumulate between the plane of the first and second electrodes and the plane of the inter-electrode zone. In addition, this configuration makes it possible to promote the passage of current in the skin and not through the formula situated on the plane of the first and second electrodes for iontophoresis.

According to a characteristic of the invention, the device comprises a body containing the storage means and an applicator head mounted on the body. This configuration promotes the compactness of the application device and the simplicity of use and handling.

According to yet another characteristic of the invention, the first electrode and the second electrode for iontophoresis are arranged in the applicator head so as to provide a compact device and avoid leakage currents.

According to yet another characteristic of the invention, the first and second electrodes for iontophoresis and the pair of electrodes for the measurement of impedance are independent so as not to create interference in their operation.

In order to permit rapid supply of product to be distributed, and to provide a compact device, easy to maintain and handle, the means of storing the product to be distributed comprises a cartridge removably connected to the body of the application device.

The invention also concerns a process for detecting the absence of product to be distributed in a distribution cavity of a product application device according to any one of the aforementioned characteristics. The process including the following steps measurement via the measuring means of a value of a physical or physicochemical parameter in the distribution cavity;

transmission of this measured value to the electronic control circuit;

comparison, by the electronic control circuit, of this measured value of the physical or physicochemical parameter with a threshold reference value;

detection, by the electronic control circuit, of the absence of product in the distribution cavity.

5. LIST OF FIGURES

Other innovative characteristics and advantages will be seen in the following description, provided for reference and in no way restrictive, in reference to the attached drawings, in which.

6. DETAILED DESCRIPTION

Figure 1:
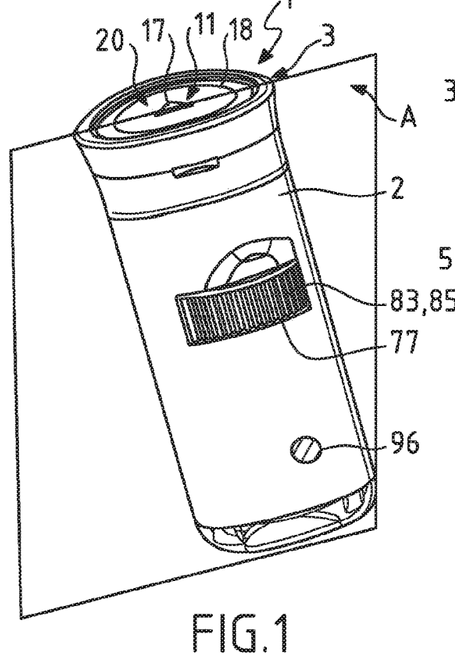
FIG. 1 is a perspective view of a device for applying a product to be distributed on a user's skin by iontophoresis according to the invention.

In reference to FIG. 1, the device 1 for applying a product to be distributed on a user's skin by iontophoresis according to the invention is intended for cosmetic and/or therapeutic treatment of the user's skin. The device 1 here uses the principle of iontophoresis, an electrophoresis principle, to promote and facilitate the penetration of the product and its active ingredients through the user's skin. Iontophoresis, here, is the application of an electric field through the skin acting as a driving force to permit the displacement of the product's ions. The skin is treated in a non-invasive manner.

The device comprises a body 2 forming a gripping device of the device 1 and an applicator head 3 mounted on the body 2. As visible in FIG. 2, the device comprises at least one means 84 for storing the product to be distributed on the skin. Advantageously, but not restrictively, the body 2 comprises the means 84 for storing the product to be distributed. As for the applicator head 3, it comprises at least one means 11 for distribution of the product to be distributed on the user's skin.

The term "product" within the meaning of the invention refers to a product in the form of a fluid such as a liquid and/or an aqueous composition. The product includes active ingredients able to provide care or treatment via the skin.

Figure 2:
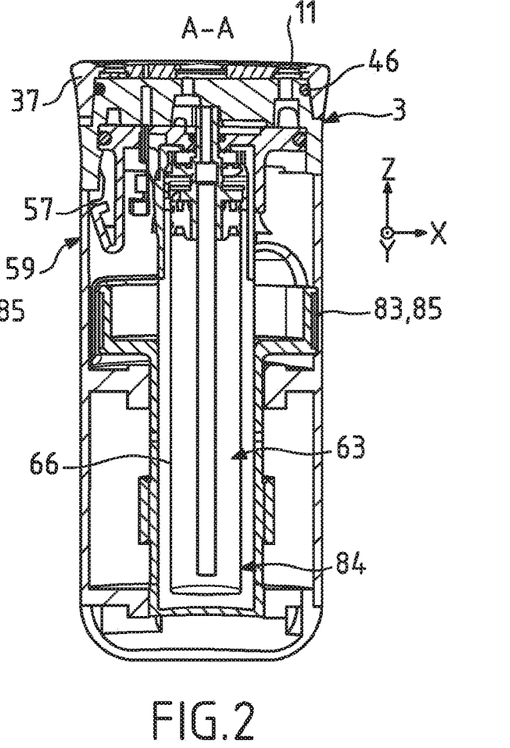
FIG. 2 is a longitudinal cross-sectional view of the product application device according to the cutting plane A-A in FIG. 1.
Figure 3:
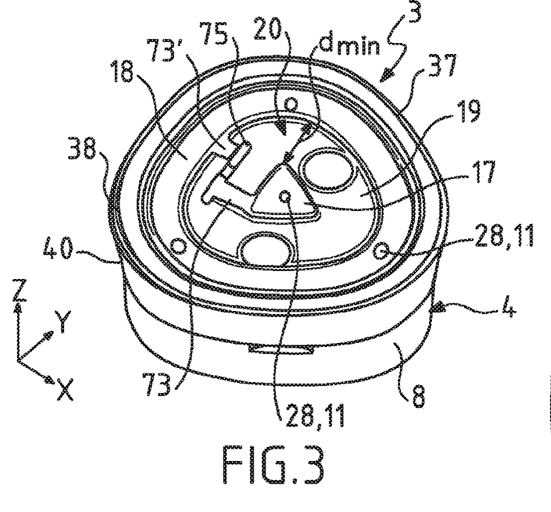
FIG. 3 is a top perspective view of an example of an applicator head of a product application device according to the invention.
Figure 4:
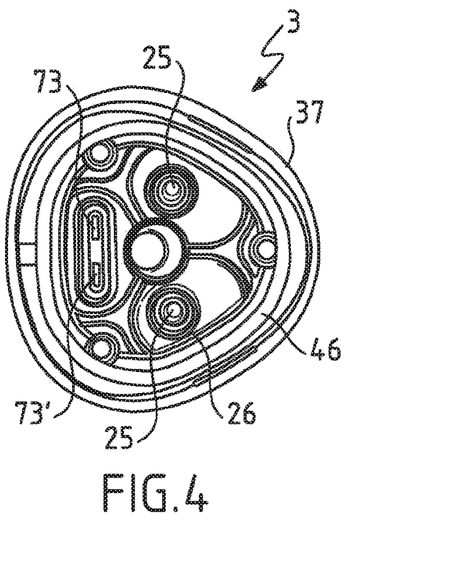
FIG. 4 is a bottom view of the example of the applicator head illustrated in FIG. 3.

In reference to FIGS. 2 to 7, the applicator head 3 is removably mounted on the body 2 so as to permit replacement of the head in the event of deterioration and/or damage, and thus to facilitate its cleaning. The applicator head 3 as illustrated in FIGS. 3 and 4 comprises an upper interface intended to be oriented toward the user's skin and an opposite lower interface intended to be connected to the body 2 of the product application device.

To facilitate comprehension of the invention, we consider that the applicator head 3 extends along a vertical longitudinal axis Z. A horizontal axis X is also represented, which is perpendicular to the vertical longitudinal axis Z and to the transverse axis Y such that these three axes X, Y, Z form a right-handed coordinate system as illustrated in FIGS. 2 and 3, for example. The terms "lower," "upper," "high," "low," "top," and "bottom" are defined with reference to the vertical longitudinal axis Z and the term "lateral" is defined with reference to the horizontal axis X.

Figure 5:
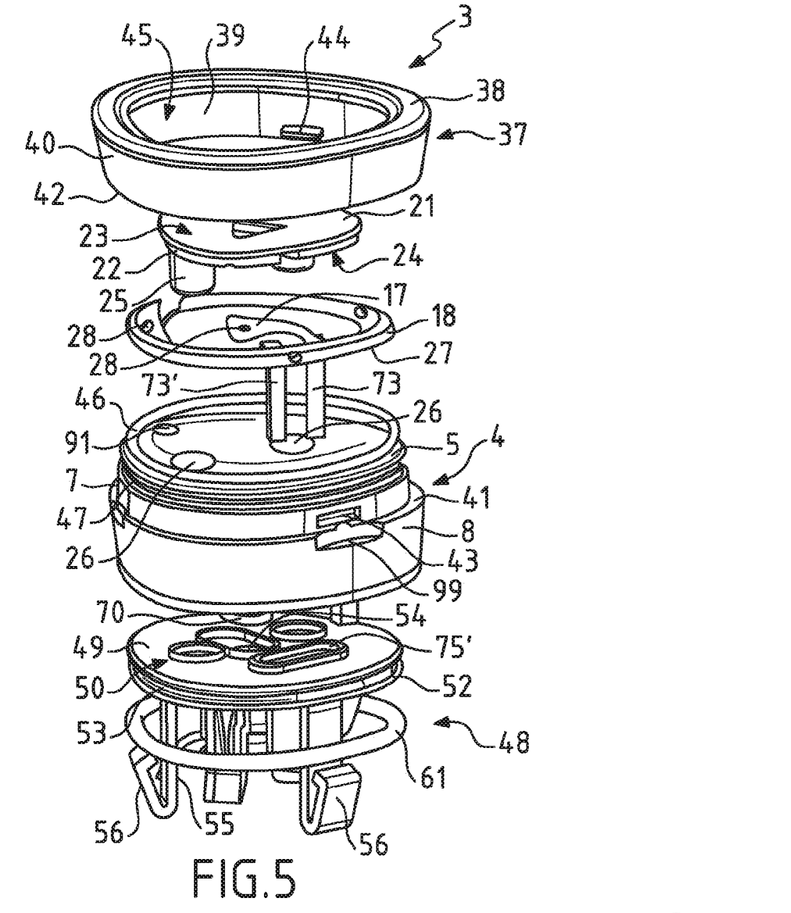
FIG. 5 is an exploded perspective view of an example of an applicator head of an application device according to the invention.
Figure 6:
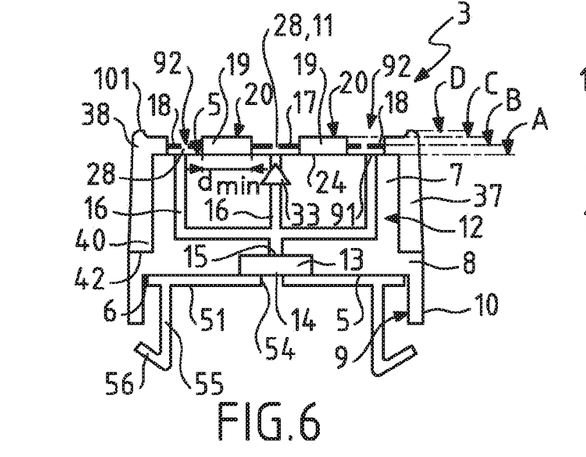
FIGS. 6 and 7 illustrate, schematically and in more detail, a sectional view of two examples of applicator head according to the invention.
Figure 7:
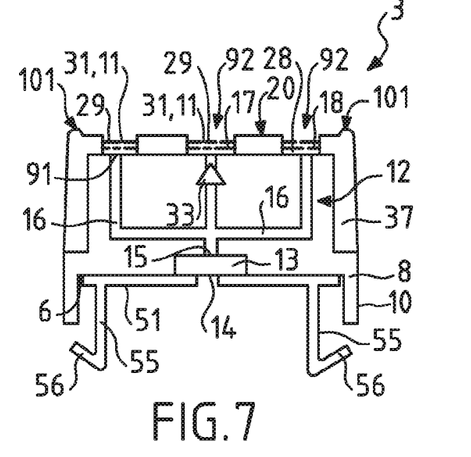

Illustrated more precisely in FIGS. 5, 6 and 7, the applicator head 3 comprises a base 4 comprising an upper surface 5 and a lower surface 6 connected by a wall 7. This wall 7 is extended by a side skirt 8 which extends toward the bottom, according to the axis Z, from the periphery of the wall 7. The side skirt 8 has an inner surface 9 and an opposite outer surface 10 along its length. The base 4 has a roughly triangular cross-section. Of course, the base 4 may have a circular or other cross-section when compatible with the body of the application device 1.

On FIGS. 6 and 7, the base 4 also comprises a circuit 12 for distribution of the product to be distributed arranged between the upper surface 5 and the lower surface 6. In particular, the distribution circuit 12 comprises, at the lower surface 6 of the base 4, a buffer reservoir 13 intended to receive or collect the product from the body 2 of the application device 1. The buffer reservoir 13 has an inlet 14 receiving the product to be distributed from the body 2 and an outlet 15 permitting the product to circulate toward the means 11 for distribution of the product on the skin. To permit the product to circulate toward the distribution means 11, the distribution circuit 12 comprises distribution channels 16 connecting the means 11 for distribution of the product and the buffer reservoir 13. The distribution channels 16 are formed in the wall 7 of the base 4. The distribution channels end at the upper surface 5 of the base 4 with distribution openings 91 and in particular they permit connecting the outlet 15 of the buffer reservoir 13 with these distribution openings 91. Advantageously, but not restrictively, each distribution opening 91 communicates fluidically with a distribution channel 16 of the distribution circuit 12.

The application device comprises at least one first electrode 17 able to generate an electric current so as to permit an active ingredient of the product to penetrate the skin. In the context of the invention, the device comprises at least one second electrode 18 for iontophoresis. These first and second electrodes 17, 18 are each installed in at least one distribution cavity 92 contained by the application device 1 and able to receive the product to be distributed. In particular, the distribution cavity 92 is formed in the applicator head 3 and is in fluidic communication with at least one distribution opening 91. We observe more precisely on FIGS. 6 and 7 that the first electrode 17 and the second electrode 18 are arranged over the upper surface 5 of the base 4. The first electrode 17 and the second electrode 18 are connected to an electric current generator (described later in the description) so as to produce an electric current which is intended to cause the penetration of the product to be distributed in the skin. The first electrode 17 and the second electrode 18 for iontophoresis are separated from each other by an inter-electrode zone 19 ensuring a constant space between the first and second electrodes 17, 18. The inter-electrode zone 19 comprises an application surface 20 intended to be in contact with the skin in order to apply the product to be distributed. In other words, the first and second electrodes 17, 18 are set back from the said inter-electrode zone 19, so that the said first and second electrodes are not in contact with the user's skin. More precisely, the inter-electrode zone 19 is advantageously, but not restrictively, formed by an assembly member having a base 21 with a side wall 22 connecting a first surface 23 oriented toward the user's skin, which thus defines the application surface 20 and a second surface 24 which is opposite it. The assembly member here has two pins 25 which extend from the second surface 24 and which are intended to fit into two corresponding holes 26 of the base 4 so as to permit the assembly member to fit into the base 4. The holes 26 cross the base 4 from the upper surface 5 to the lower surface 6 of the base 4 (see FIG. 4). Since the side wall 22 has a certain thickness, the application surface 20 is situated at a distance from the upper surface 5 of the base 4. In particular, the upper surface 5 of the base 4 is defined in a plane A, while the first and second electrodes 17, 18, being arranged over the upper surface 5, are defined in a plane B parallel to the plane A. As for the inter-electrode zone 19, and in particular, the application surface 20, this is defined in a plane C which is parallel to the plane B of the first and second electrodes 17, 18. The plane B of the first and second electrodes 17, 18 and the plane C of the inter-electrode zone 19 are situated at a predetermined distance from each other. The predetermined distance is between 0.3 and 1.3 millimeters (mm). According to a particular characteristic of the invention, the inter-electrode zone 19 has a predetermined minimum distance dmin between the first electrode 17 and the second electrode 18. This predetermined minimum distance dmin is advantageously between 5 mm and 20 mm. Preferably, but not restrictively, this distance dmin is 10 mm. The distribution cavity 92 is thus obtained because of the distance separating the plane B from the first and second electrodes 17, 18 and the plane C from the inter-electrode zone 19. The latter therefore has at least one bottom formed by the upper surface 5 of the base 4 and the side walls formed by the side wall 22 of the assembly member (inter-electrode zone 19). The side walls of the cavity 92 may also be formed of an inner wall of a collar 38 of a cap 37 contained by the applicator head 3 described below. The cavity 92 of the applicator head 3 permits the formation of a thin film of product to be distributed in this cavity 92. In other words, the accumulation of product is avoided on the upper interface of the applicator head.

Advantageously, but not restrictively, the distribution means 11 comprises one or more product outlet openings toward the user's skin, ending at the upper interface of the applicator head 3.

According to a characteristic of the invention, the first electrode 17 and the second electrode 18 each have a wall 27 with perforations 28.

According to a first embodiment illustrated in FIG. 6, the perforation or perforations 28 distribute the product toward the user's skin. In other words, the perforations 28 constitute the one or more product outlet openings toward the skin. Thus, the product circulates through the distribution opening 91 of the base 4 toward the perforations 28 of each first and second electrode 17, 18. In this embodiment, the first and second electrodes are made of an electrically conductive material. This electrically conductive material may comprise a metallic material or a polymer or a composite material containing this polymer material. The polymer may be a polytetrafluoroethylene (PTFE). The metallic material may be a stainless steel.

Figure 16:
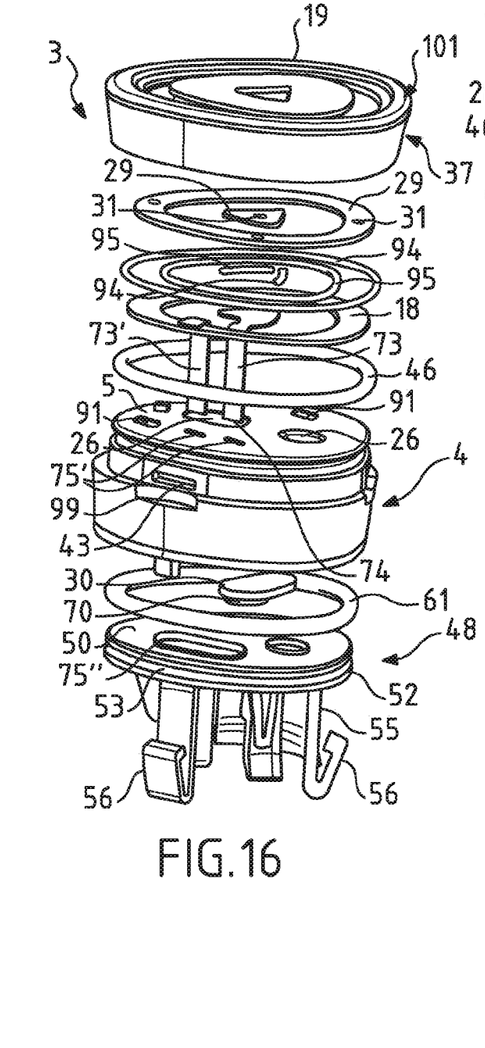
FIG. 16 represents an embodiment of the invention on which is represented an example embodiment of the applicator head in burst view with measuring means.

According to a second embodiment illustrated in FIG. 7, as well as another embodiment illustrated in FIG. 16, at least one plate 29 presenting a wall with perforations 31 is arranged in the applicator head 3 of the application device 1. More precisely, the plate 29 is arranged above each first and second electrode 17, 18. In this case, the product circulates through the one or more distribution openings 91, the one or more perforations 28 of the first and second electrodes 17, 18 toward the perforations 31 of the plate 29, which distribute the product toward the user's skin. Advantageously, this plate 29 is not conductive, in order to avoid irritation or tingling on the user's skin. The plate 29 may be made of a polymer material. Preferably, but not restrictively, the polymer is a thermoplastic such as a polytetrafluoroethylene (PTFE) or a polyoxymethylene (POM). In this embodiment, the first and second electrodes 17, 18 for iontophoresis are made of a composite material. Advantageously, the composite material may be a carbon-filled polymer.

Figure 8:
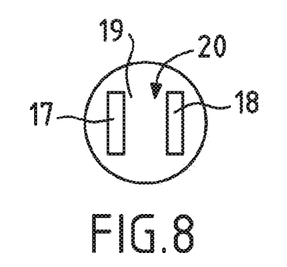
FIGS. 8 to 10 schematically represent embodiments of the arrangement of the first and second electrodes in the applicator head.
Figure 9:
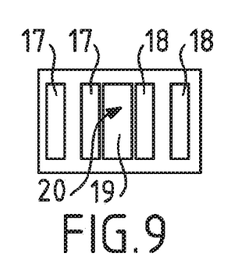
Figure 10:
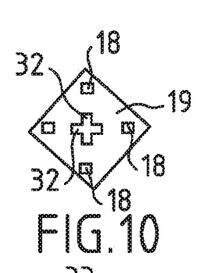

The first and second electrodes 17, 18 may be arranged in various ways above the upper surface 5 of the base 4. In one embodiment, as illustrated on FIGS. 1, 3, 6 and 7, the first electrode 17 is arranged at the center of the base 4. As for the second electrode 18, it is arranged at the periphery of the applicator head 3, more precisely, around the perimeter of the inter-electrode zone 19. The first electrode 17 illustrated has a roughly triangular shape. The second electrode 18, in this embodiment, has a closed contour with a generally triangular shape. In another embodiment, illustrated in FIG. 8, the first and second electrodes 17, 18 for iontophoresis have a rectangular shape. These are arranged parallel to each other and are separated by the inter-electrode zone 19. According to another embodiment illustrated in FIG. 9, the first and second electrodes 17, 18 are rectangular in shape. The electrodes are four in number and they are arranged at a distance from each other. The inter-electrode zone 19 is arranged at the center of the applicator head 3 such that there are, for example, two first electrodes 17 to the left of the inter-electrode zone 19 and two second electrodes 18 to the right of the inter-electrode zone 19. According to yet another embodiment illustrated in FIG. 10, the first electrode 17 has the general shape of a cross with two perpendicular branches forming four edges 32. The first electrode 17 is arranged at the center of the head 3, and in particular at the center of the upper surface 5 of the base 4. Some second electrodes 18, in this case four of them, are arranged at a distance from the first electrode 17 and around the latter. Each second electrode 18 is arranged in line with the extension of an edge 32 of the first electrode 17. The inter-electrode zone 19 separates the first and second electrodes 17, 18. Other configurations of the first and second electrodes 17, 18 are, of course, possible.

In the various embodiments described, the applicator head 3 comprises at least one electrical insulation means 33 which is fluidically interposed between the first electrode 17 and the second electrode 18. This electrical insulation means 33 is configured so as to permit or limit, or even prevent, the passage of electric current between the first electrode 17 and the second electrode 18 via the applicator head 3. In reference to FIGS. 6 and 7, the insulation means 33 is arranged on one of the distribution channels 16. In order to be able to control the circulation of electric current between the first electrode 17 and the second electrode 18, the electrical insulation means 33 is arranged on the distribution channel 16 which leads towards the first electrode 17, between the distribution opening 91 and the outlet 15 of the buffer reservoir 13. In fact, on FIGS. 6 and 7, the first electrode 17 for iontophoresis is situated at the center of the applicator head 3 while the second electrode 18 for iontophoresis surrounds the periphery of the first electrode 17, and in particular, the inter-electrode zone 19.

Advantageously, but not restrictively, the electrical insulation means 33 is situated close to the distribution opening 91 of the distribution channel 16 leading to the first electrode 17 in order to limit as much as possible the leakage currents toward the second electrode 18 via the applicator head 3.

To permit or limit the passage of current between the first electrode 17 and the second electrode 18 via the applicator head 3, the electrical insulation means 33 is able to be in an open position or a closed position. In the closed position, the current circulates only between the first electrode 17 and the second electrode 18. In the open position, the current circulates in a limited manner in the applicator head 3 and in the body 2. The electrical insulation means 33 has a clearance area which, when the electrical insulation means 33 is in the open position, permits the circulation of electric current between the first and the second electrodes 17, 18 and in the distribution channels 16 of the applicator head 3. Nevertheless, this clearance area is so small that the impedance of the path to travel is too great to favor circulation of current via this clearance area. Thus, the electric current circulates almost exclusively in the upper interface (skin side) rather than toward the interior of the applicator head 3 and the body 2.

In the open position, the product to be distributed circulates from the body 2 toward the first and second electrodes 17, 18, while in the closed position, the product no longer circulates toward the first electrode 17. Once the product is again extracted from the storage means 84, toward the buffer reservoir 13, the pressure of the product causes the electrical insulation means 33 to open such that the first and second electrodes 17, 18 for iontophoresis are supplied with product. The opening pressure of the electrical insulation means 33 is chosen appropriately in relation to the distribution channels 16 supplying the second electrode 18 and the associated pressure loss. Ideally, the pressure loss undergone by the product to be distributed in the passage of the insulation means 33 is equal to the pressure loss of the longer distribution channels 16 supplying the second electrode 18. Alternatively, electrical insulation means 33 may also be arranged on the distribution channels 16 leading to the second electrode 18 for iontophoresis. This advantageously permits balancing the product's circulation toward the first and second electrodes 17, 18 for iontophoresis, and thus optimizing equal supply of product to the first and second electrodes 17, 18 for iontophoresis.

Figure 11:
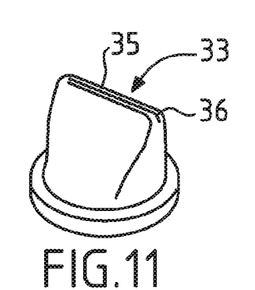
FIGS. 11 to 13 represent an example of electrical insulation means to be interposed between the first electrode and the second electrode.
Figure 12:
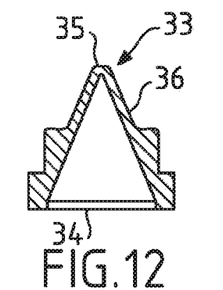
Figure 13:
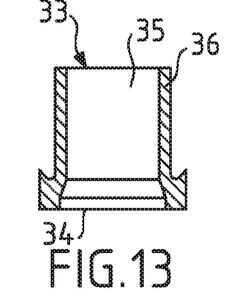

In addition, the insulation means 33 is in the open position when a pressure inside the insulation means 33 reaches a predetermined threshold. Advantageously, but not restrictively, the insulation means 33 is a valve, and preferably, a check valve as illustrated in FIGS. 11 to 13. However, the insulation means 33 may take another form. The valve comprises a body with a first end at which an entry 34 is formed and an opposite second end at which an exit 35 is formed. The exit 35 is in the form of a duck's bill formed of two opposite lips 36 that are elastically deformable. The two lips 36 open if the pressure value inside the valve is at least equal to a predetermined pressure threshold value, and they close when the pressure value inside the valve is lower than the predetermined pressure threshold value. The predetermined pressure threshold value is between 5 and 200 millibars (mbar). Preferably, but not restrictively, the predetermined threshold pressure value is approximately 50 mbar. It should be noted that in the open position, the clearance area of the lips 36 formed at the outlet 35 is very low, and consequently the impedance is high. The maximum clearance area (of opening) of the lips 36 is between 0.2 mm² and 2.5 mm². Thus, the circulation of the product to be distributed is possible, but that of the current is limited between the first electrode 17 and the second electrode 18 for iontophoresis via the applicator head 3.

The valve is made of a polymer material, such as silicone.

The applicator head 3 comprises the cap 37 or cover secured to the base 4 to hold the first and second electrodes 17, 18 in position in the applicator head 3. The cap 37 comprises the collar 38 which has a central opening 39 through which the base 4 is received. The first and second electrodes 17, 18 as well as the assembly member (application surface 20) are visible through this central opening 39. The collar 38 has an upper surface 101 which is defined in a plane D. This upper surface 101 forms a support ring whose purpose is to create a volume with a low thickness on the skin. This plane D is roughly parallel to the plane C of the application surface 20 of the inter-electrode zone 19. The plane D is also parallel to the plane B of the first and second electrodes 17, 18 for iontophoresis. The collar 38 of the cap 37 includes in its periphery a side skirt 40 intended to cooperate with the wall 7 of the base 4. In particular, between the side skirt 8 and the wall 7 of the base 4, there is provided a flange 41 on which rests a free end 42 of the side skirt 40. The wall 7 of the base 4 also has blind slots 43 (see FIGS. 5 and 16) in each of which a ledge 44 is mounted on an inner wall 45 of the side skirt 40 to attach the cap 37 to the base 4. To facilitate the disassembly of the cover 37 of the base 4, the base includes a notch 99 on the wall 7. The notch is situated close to each blind slot 43 and allows the user's finger to access the free end 42 of the cover 37.

Between the inner wall 45 of the side skirt 40 of the cap 37 and the wall 7 of the base 4 is arranged a first gasket 46. In order for the first gasket 46 to be held in position, the wall 7 of the base 4 includes a groove 47 extending in the direction of the perimeter of the wall 7. The first gasket 46 has a ring-shaped body. Advantageously, the first gasket 46 is made of an elastically deformable material. This deformable material is preferably a polymer or a copolymer chosen from one of the following: an ethylene propylene diene monomer (EPDM), a fluorocarbon rubber (FPM), a polyacrylic elastomer (ACM), an ethylene-acrylic copolymer (AEM), a hydrogenated nitrile rubber (HNBR), a VITON®, or a butyl.

The applicator head 3 further comprises a connecting member 48 to removably connect the applicator head 3 and the body 2 (see FIGS. 5 and 16). This connecting member 48 comprises a support part 49 which includes an upper face 50 and a lower face 51 connected by a wall 52. The support part 49 has an opening 54 going through the wall 52 on both sides. This opening 54 communicates with the entrance 14 of the buffer reservoir 13. The support part 49 is equipped with fixing brackets 55, three of them here, which extend from the inner face 51 of the support part 49. The support part 49 is force fit with the inner surface 9 of the side skirt 8 of the base 4. The fixing brackets 55 have roughly a V shape toward each of their free ends 56. These fixing brackets 55 cooperate with a bulge 57 provided at a proximal end 58 of a first portion 59 of the body 2. The bulge 57 is arranged on an inner surface 60 of the body 2. The wall 52 is provided with a groove 53 extending along the perimeter of the wall 52 and in which a second gasket 61 is installed. The gasket 61 is in contact with the inner surface 9 of the side skirt 8.

Advantageously, the product to be distributed is contained in a cartridge 63 which is removably connected to the body 2 of the device. Thus, when the product is exhausted, the cartridge 63 may easily be replaced or refilled.

Figure 14:
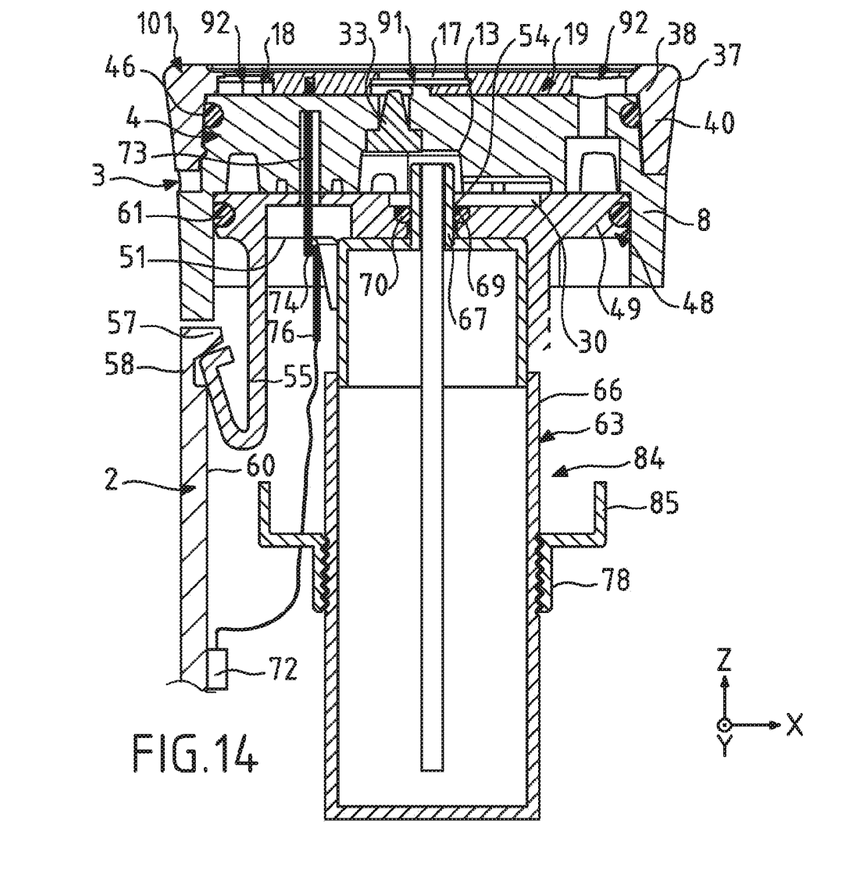
FIG. 14 is a partial sectional and detail view of an example of an applicator head mounted and connected on an application device body which includes a cartridge according to the invention.
Figure 20:
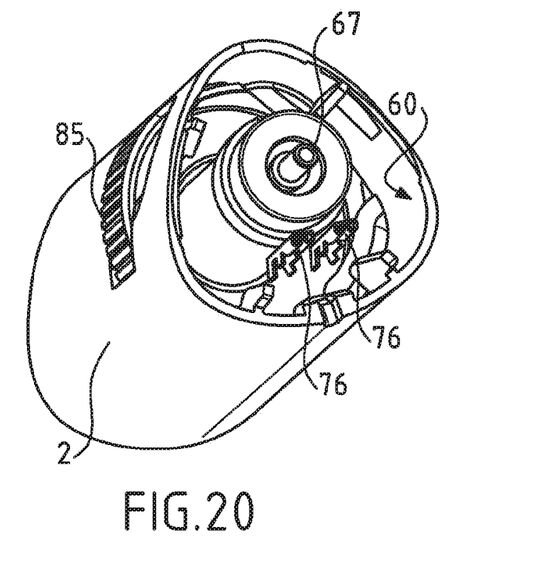
FIG. 20 illustrates a top perspective view of a connection portion of the device body intended to connect with an applicator head according to the invention; and, FIG. 21 is an example of a simplified block diagram representing the different communications of the electronic control circuit between the means for measuring physical or physicochemical parameters in the distribution cavity, the alert means, the current generator and the means for extracting the product to be distributed.
Figure 21:
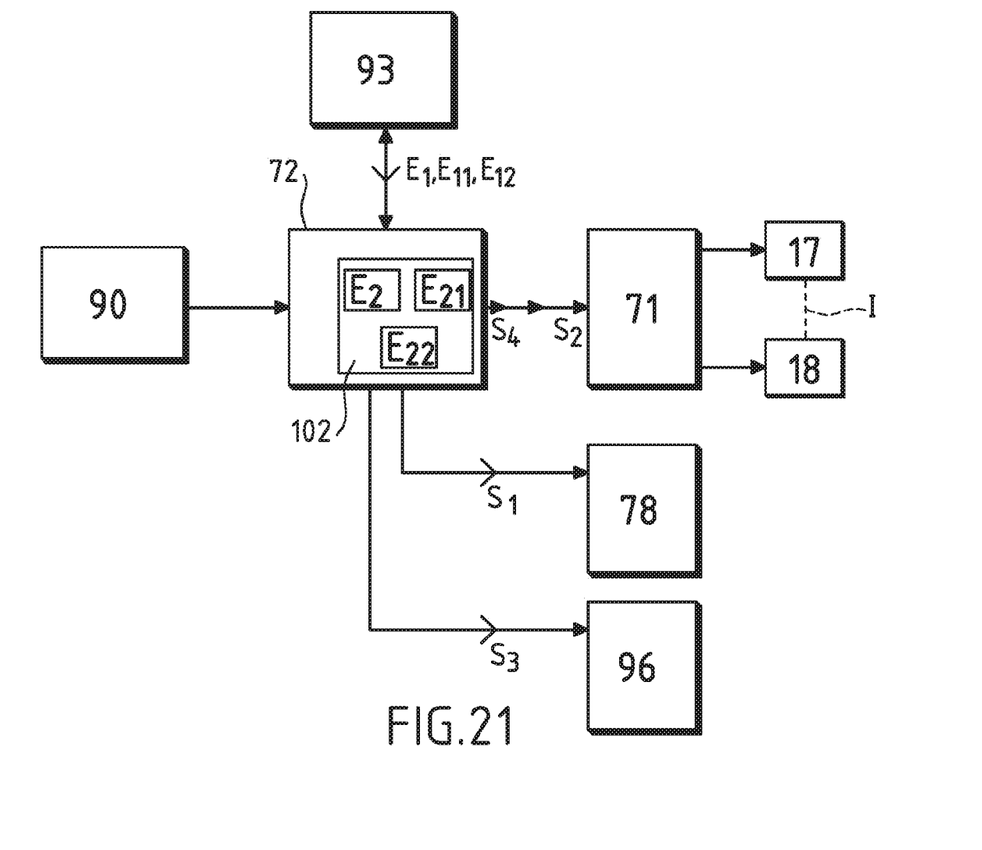

In reference to FIGS. 14 and 20, the cartridge 63 comprises a housing 66 receiving an attaching head 67. The attaching head 67 is inserted through the opening 54 of the connecting member 48 and a portion of the attaching head extends in the buffer reservoir 13. The attaching head 67 is attached in relation to the applicator head 3. A gasket 70 is also housed in a groove 69 of the support part 49 of the connecting member 48. The gasket 70 is fixed in the groove 69 by a stop 30 such that the product to be distributed does not intersect the attaching head 67 of the cartridge 63.

The body 2 comprises at least one extraction means 78 to permit extracting the product in the storage means 84 from the body 2. This extracting means 78 may be manual or motorized. In manual mode, the device may comprise a drive means 82 comprising a portion 83 (see FIG. 1) extending through the opening 77 of the body 2 of the device 1 so that the user can activate it easily. Advantageously, but not restrictively, this drive means 82 comprises a wheel 85.

As a variant, the motorized extraction means 78 comprises a motor (not represented) activating means to permit rotating the distribution mechanism. The motor may be activated via a button (not represented) accessible on the body 2 of the application device 1. This button is connected to an electronic control circuit 72 to activate the motor.

Figure 15:
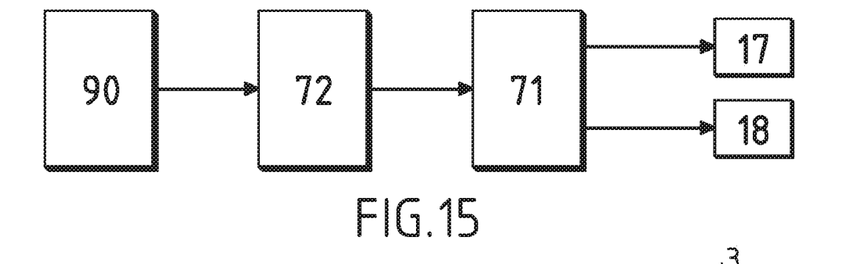
FIG. 15 is an example of a simplified block diagram representing the electrical communications between an electronic control circuit, a current generator and the first and second electrodes.

In the body 2 is also arranged a current generator 71 to permit delivering a low-intensity current to the first and second electrodes 17, 18 arranged in the applicator head 3. The electric current is between 50 microamperes (μA) and 6000 μA. Preferably, but not restrictively, the electric current is approximately 800 μA. The current may be alternating or direct. The electric current generator 71 is controlled by the electronic control circuit 72 installed in the body 2 of the product application device 1 to provide the current. The electronic control circuit 72 is powered by an electric power source 90 that may be a battery or a rechargeable battery on a household power supply grid. This is illustrated in a block diagram in FIG. 15. Alternatively, the device 1 may comprise an electric power cord (not represented) intended to be connected to the household power supply grid and to power the electronic control circuit 72. To ensure an electrical connection between the current generator 71 and the first and second electrodes 17, 18, these electrodes are each equipped with a pin 73, 73' (see FIGS. 5, 14 and 16). The pins 73, 73' and the first and second electrodes 17, 18 are formed here of a single piece (in one piece). Each pin 73, 73' (see FIGS. 14 and 16) has a free end 74 accessible from the lower interface of the applicator head 3. In other words, each pin 73, 73' crosses the inter-electrode zone 19, the base 4 and the connecting member 48 on both sides via slits 75, 75', 75" contained by the latter. The pins 73, 73' are thus accessible from the lower face 51 of the connecting member 48 of the applicator head 3. Each pin 73, 73' has a length superior to the lengths of the inter-electrode zone, the base 4 and the connecting member 48. Here, each of the pins 73, 73' has a section in the shape of a backwards L. The body 2 of the device comprises connecting elements 76 which are connected to the current generator 71. One connecting element 76 is connected to the anode of the current generator 71 and another connecting element 76 is connected to the cathode of the current generator 71. As such, when the applicator head 3 is connected to the body 2 of the device 1, each pin 73, 73' cooperates with a connecting element 76 and is supplied with electric current.

According to a characteristic of the invention, when the product is distributed, a closed circuit is formed with the user's skin, the first electrode 17 for iontophoresis and the second electrode 18 for iontophoresis. In order to avoid skin microlesions creating sensations of discomfort or even pain in the case of strong intensity or prolonged duration, or to detect a problem with functioning or tolerance, the device may include a temperature probe. Advantageously, this temperature probe is integrated in the applicator head 3 of the application device 1 and connected to the electronic control circuit 72.

In another embodiment as illustrated in FIGS. 16 to 19 and 21, the application device 1 comprises means 93 for measuring a physical or physicochemical parameter which are connected to the electronic control circuit 72. These measuring means 93 are configured so as to send a parameter measurement signal $E_1$ to the electronic control circuit 72. In this embodiment, the electronic control circuit 72 is configured to compare the measured value of the physical or physicochemical parameter with a threshold reference value so as to detect an absence of product in the distribution cavity 92. Advantageously but not restrictively, the electronic control circuit 72 comprises a memory 102 in which the threshold reference value is stored. The electronic control circuit 72 also comprises a comparator (not represented) intended to compare the threshold value with the value measured by the measuring means 93.

Figure 17:
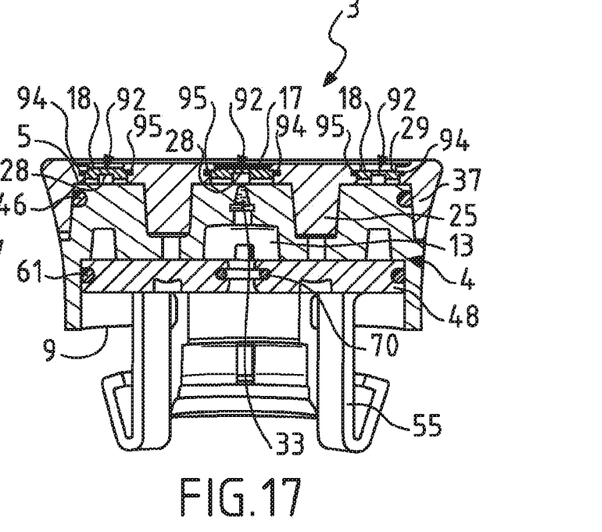
FIG. 17 is a sectional view of the applicator head of the embodiment illustrated in FIG. 16.
Figure 18:
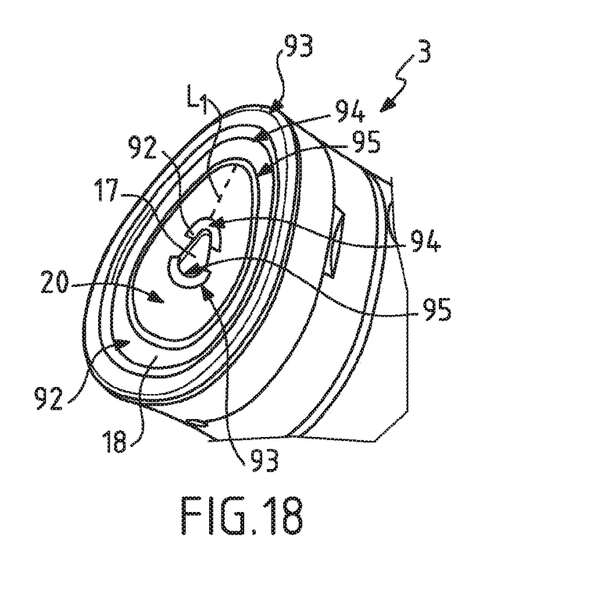
FIG. 18 is a partial and perspective view of an applicator head according to the invention, comprising measuring means according to an example embodiment.

According to a first embodiment illustrated in FIGS. 16 to 18, the measuring means 93 comprise a means for measuring impedance in the distribution cavity 92. This impedance measuring means is located in at least one distribution cavity 92. Here, this impedance measuring means comprises a pair of electrodes which are arranged in each distribution cavity 92 and between which an electric current may circulate. Each pair of electrodes comprises a first transmitting electrode 94 able to emit an electric current $I_1$ and a second receiving electrode 95 able to receive the electric current $I_1$ transmitted by the first transmitting electrode 94. The first transmitting electrode 94 and the second receiving electrode 95 are connected to a voltage generator (not represented). Each of the first transmitting electrode 94 and the second receiving electrode 95 is realized by overmolding during manufacture of the assembly member 19 and/or of the cap 37 in order to facilitate the mounting of these electrodes. Of course, it may be possible to make the electrodes using a screen printing process or other similar methods. Advantageously, the first and second electrodes 17, 18 for iontophoresis and the electrodes 94, 95 for the measurement of impedance are independent. The electrodes 94, 95 for the measurement of impedance are made of the same material(s) as the first and second electrodes 17, 18 for iontophoresis. The first transmitting electrode 94 is arranged facing the second receiving electrode 95. The electric current $I_1$ is transmitted by the first transmitting electrode 94 to the second receiving electrode 95. Then, the value of the intensity of this electric current $I_1$ is converted to a corresponding measured impedance value. This impedance value inside the distribution cavity 92 corresponds, here, to the value of the measurement signal $E_1$. The measurement signal $E_1$ is transmitted to the electronic control circuit 72 which compares the value of the measurement signal $E_1$ with a predetermined impedance threshold value $E_2$. Advantageously, the electronic control circuit 72 is intended to generate at least one command signal S1, S2, S3 according to the measurement signal $E_1$.

Advantageously, but not restrictively, when the value of the measurement signal $E_1$ measured is less than or equal to a predetermined impedance threshold value $E_2$, the electronic control circuit 72 generates a command signal S1, S2, S3. Conversely, when the value of the measurement signal $E_1$ measured is greater than the predetermined impedance threshold value $E_2$, the control circuit 72 does not send a command signal. In particular, the electronic control circuit 72 sends a command signal S1, S2, S3 when there is no product in the distribution cavity 92. When the electronic control circuit 72 does not send a command signal, there is no product in the cavity 92. Of course, the electronic control circuit 72 can be configured to generate a command signal if product is present in the cavity 92. For example, the latter may emit a command signal S2 to reactivate the power supply of the first and second electrodes 17, 18 for iontophoresis.

Thus, when there is no product in the distribution cavity 92, the electronic control circuit 72 sends the following command signals:

a command signal S1 able to trigger distribution of product in the distribution cavity 92;

a command signal S2 intended to generate an electric current able to circulate in the first and second electrodes 17, 18 for iontophoresis; or a command signal S3 able to alert the user to the absence of product in the distribution cavity 92.

In the case of the command signal S1, the latter activates the motor activating the drive means of the cartridge 63 in the body 2 of the device.

In the case of the command signal S2, the latter reactivates the current generator 71 to generate an electric current in the first and second electrodes 17, 18 for iontophoresis. In fact, when the measurement is taken in the distribution cavity 92 by each pair of impedance measurement electrodes, the first and second electrodes 17, 18 for iontophoresis are not active. For this, the electronic control circuit 72 is configured to send a command signal S4 to cut the electric power of the first and second electrodes 17, 18 for iontophoresis during the measurement.

In the case of the command signal S3, the application device 1 comprises alert means 96 connected to the electronic control circuit 72 to alert the user to the absence of product in the distribution cavity 92. The alert means 96 may be visual and/or audible means. The user thus alerted will consequently decide if the treatment or care of the skin is finished, in which case he will not activate the means 78 for extracting the product to be distributed. In the alternative, the user will activate the extraction means 78.

Figure 19:
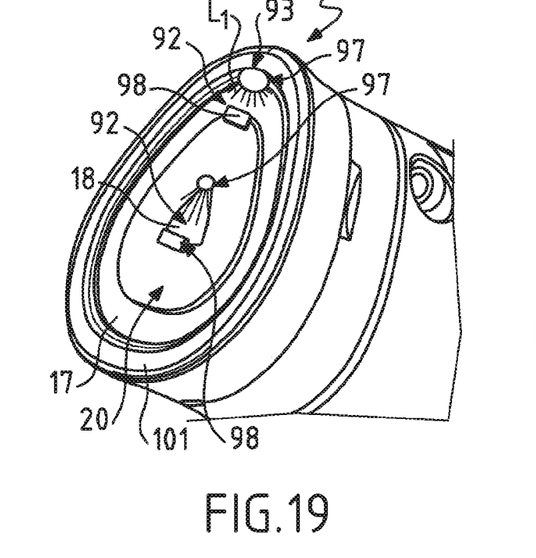
FIG. 19 represents a partial and perspective view of an applicator head according to the invention, with measuring means according to another example embodiment.

According to a second embodiment illustrated in FIG. 19, the measuring means 93 comprise an optical measuring means. This optical measuring means is ideally located in the cavity 92 for distributing the product to be distributed. The optical measuring means of the product permits transmitting information representative of the light intensity inside the distribution cavity 92. The optical measuring means is connected to the electronic control circuit 72 which is able to process the information representative of the light intensity inside the distribution cavity 92. For this, the optical measuring means comprises at least one light beam transmitter 97 and at least one light beam receiver 98 arranged facing the light transmitter 97. The transmitter 97 has a light source able to transmit a light beam $L_1$ and arranged on one side of the distribution cavity 92. This light source includes, for example, a light-emitting diode (abbreviated LED) which transmits wavelengths between 500 and 1500 nm. The receiver 98 has a light receiver able to receive the light beam $L_1$ transmitted by the light source and is placed on the other side of the distribution cavity 92. The receiver 98 of the light beam comprises a photocell receiving the wavelength(s) transmitted by the LED and able to transform it or them into an electric current. In this embodiment, the optical measuring means takes a first measurement in order to detect whether the device is in contact with the user's skin. In the context of this first measurement, the light beam L1 is transmitted by the transmitter 97 to the receiver 98. Then, the light beam $L_1$ is converted to electric current representative of the light intensity received. This light intensity value inside the distribution cavity 92 corresponds, here, to the value of the measurement signal $E_{11}$. The measurement signal $E_{11}$ is transmitted to the electronic control circuit 72 which compares the value of the measurement signal $E_{11}$ with a predetermined light intensity threshold value $E_{21}$. Advantageously, the electronic control circuit 72 is intended to generate a first command signal or a second signal according to the measurement signal $E_{11}$.

Advantageously, but not restrictively, when the value of the measurement signal $E_{11}$ measured is less than the predetermined light intensity threshold value $E_{21}$, the electronic control circuit 72 generates a first command signal. Conversely, when the value of the measurement signal $E_{11}$ measured is greater than or equal to the value of the predetermined light intensity threshold value $E_{21}$, the control circuit 72 sends a second command signal. In particular, the electronic control circuit 72 sends the first command signal when the device is in contact with the user's skin and the second command signal when the device is not in contact with the skin.

When the electronic control circuit 72 detects that the device 1 is in contact with the skin, the electronic control circuit sends to the optical measuring means the first command signal able to trigger a second measurement. This second measurement permits detecting if there is no product in the distribution cavity 92. For this, a measurement signal $E_{12}$ represents a value of light intensity inside the distribution cavity 92. The measurement signal $E_{12}$ is transmitted to the electronic control circuit 72 which compares the value of the measurement signal $E_{12}$ with a predetermined light intensity threshold value $E_{22}$. Advantageously, the electronic control circuit 72 is intended to generate a command signal S1, S2, S3 according to the measurement signal $E_{12}$. When the value of the measurement signal $E_{12}$ measured is less than or equal to the predetermined light intensity threshold value $E_{22}$, the electronic control circuit 72 does not generate a command signal. Conversely, when the value of the measurement signal $E_{12}$ measured is greater than the predetermined light intensity threshold value $E_{22}$, the control circuit 72 generates a command signal S1, S2, S3. In particular, the electronic control circuit 72 transmits a command signal S1, S2, S3 when there is no product in the distribution cavity 92. When the electronic control circuit 72 does not transmit a command signal, product is present in the cavity 92. Of course, the electronic control circuit 72 can be configured to generate a command signal if product is present in the cavity 92. Thus, when there is no product in the distribution cavity 92, the electronic control circuit 72 sends the following command signals. These command signals are identical to the command signals generated during the impedance measurement.

a command signal S1 able to trigger distribution of product in the distribution cavity 92;

a command signal 52 intended to generate an electric current able to circulate in the first and second electrodes 17, 18 for iontophoresis; or, a command signal S3 able to alert the user to the absence of product in the distribution cavity 92;

We will now describe the functioning of the device 1 for applying a product to be distributed on the skin of a user by iontophoresis. When the application device 1 is powered up, the electronic control circuit 72 sends an order to the current generator 71 which generates an electric current I at the first and second electrodes 17, 18 for iontophoresis. The user activates the extraction means 78 until the product is extracted from the cartridge 63 and collected in the buffer reservoir 13 as a first step. As a second step, the product under pressure triggers the opening of the valve, when the pressure inside the valve reaches a predetermined value, which permits the product to pass into the distribution channels 16 formed in the base 4. The product then empties into the distribution cavity 92 via the distribution openings 91 toward the first and second electrodes 17, 18 for iontophoresis. The product going through the perforations 28 of the first and second electrodes 17, 18 for iontophoresis to the right of the electric field created is transported deep into the skin following the field lines forming a semicircular arch. The distance reached under the skin is between 2 and 10 mm deep.

According to an embodiment of the invention, the device takes measurements of physical or physicochemical parameters in the distribution cavity 92 in order to determine if there is no product in the distribution cavity 92 of the device 1. These measurements can be scheduled to take place after a predetermined time period during the operation of the device 1. First, the electronic control circuit 72 sends a command signal S4 to cut the electric power of the first and second electrodes 17, 18 for iontophoresis. Then, the electronic control circuit 72 triggers the detection process which has the following steps:
- measurement via the measuring means 93 of a value of a physical or physicochemical parameter in the distribution cavity 92;
- transmission of this measured value to the electronic control circuit 72;
- comparison, by the electronic control circuit 72, of this measured value of the physical or physicochemical parameter with a threshold reference value $E_2$, $E_{21}$, $E_{22}$; and,
- detection, by the electronic control circuit 72, of the absence of product in the distribution cavity 92.

When it is detected that there is no product in the distribution cavity 92, the electronic control circuit 72 generates a command signal S3 to alert the user to the absence of product in the distribution cavity. The user makes the decision whether to activate the extraction means 78.

Alternatively, when it is detected that there is no product in the distribution cavity 92, the electronic control circuit 72 sends a command signal such as:
- a command signal S1 able to trigger distribution of product in the distribution cavity 92; and/or,
- a command signal S2 intended to generate an electric current able to circulate in the first and second electrodes 17, 18 for iontophoresis.

The invention is described in the preceding as an example. It is understood that those skilled in the art are able to carry out different embodiment variants of the invention, for example, by combining the various above characteristics taken alone or in combination, without departing from the context of the invention.

The invention claimed is:

1. A device for applying a product to be distributed on the skin of a user by iontophoresis comprising:
   at least one storage container for storing the product to be distributed;
   at least one distribution cavity able to receive, from the at least one storage container, the product to be distributed;
   an application surface configured for direct contact with the skin of the user for applying the product on the skin;
   at least one first electrode for iontophoresis;
   at least one second electrode for iontophoresis arranged in the at least one distribution cavity;
   an electronic control circuit;
   a measuring system, for measuring a physical or physicochemical parameter, connected to the electronic control circuit and configured to send a signal indicating the parameter measurement,
   wherein the at least one first electrode for iontophoresis and the measuring system are installed in the at least one distribution cavity, the electronic control circuit being configured to compare a measured value of the physical or physicochemical parameter in the at least one distribution cavity with a threshold reference value so as to detect an absence of product in the at least one distribution cavity, wherein the at least one first electrode is set back from the application surface so that the at least one first electrode is spaced away from the skin of the user when the application surface is placed in direct contact therewith, wherein the at least one second electrode also being set back from the application surface, and wherein the at least one first electrode and the at least one second electrode for iontophoresis are separated and spaced from one another by an inter-electrode zone which comprises the application surface for applying the product on the skin.

2. The device according to claim 1, wherein the electronic control circuit is configured, when the electronic control circuit detects the absence of product in the at least one distribution cavity, to generate a command signal able to trigger distribution of product in the at least one distribution cavity.

3. The device according to claim 1, further comprising an alert system connected to the electronic control circuit, the electronic control circuit being configured, when the electronic control circuit detects the absence of product in the at least one distribution cavity, to generate a command signal able to alert the user to the absence of product in the at least one distribution cavity.

4. The device according to claim 1, further comprising at least one extraction system configured to extract the product to be distributed from the at least one storage container.

5. The device according to claim 1, wherein the measuring system comprises an impedance measuring system for measuring product impedance.

6. The device according to claim 5, wherein the impedance measuring system comprises at least one pair of electrodes for the measurement of impedance, which are arranged in the at least one distribution cavity and between which an electric current circulates.

7. The device according to claim 1, wherein the measuring system comprises an optical measuring system.

8. The device according to claim 7, wherein the optical measuring system comprises at least one light transmitter diffusing a light through the at least one distribution cavity and at least one light receiver placed opposite the transmitter.

9. The device according to claim 1, wherein the at least one first and second electrodes for iontophoresis are situated in the same plane.

10. The device according to claim 9, wherein the at least one first electrode and the at least one second electrode for iontophoresis are separated by and both set back from the inter-electrode zone which comprises the application surface for applying the product on the skin so that the at least one first electrode and the at least one second electrode are not in direct contact with the skin of the user, and wherein the inter-electrode zone is situated in a plane parallel to and spaced from said same plane of the at least one first and second electrodes, the same plane of the at least one first and second electrodes for iontophoresis being situated at a predetermined distance from the plane of the inter-electrode zone.

11. A process for detecting the absence of product to be distributed in a distribution cavity of a product application device according to claim 1, the process comprising:
   measuring via the measuring system a value of a physical or physicochemical parameter in the distribution cavity;

transmitting the measured value to the electronic control circuit;

comparing, by the electronic control circuit, the measured value of the physical or physicochemical parameter with a threshold reference value; and, detecting, by the electronic control circuit, the absence of product in the distribution cavity.

12. The device according to claim 1, wherein the at least one first electrode has a wall with perforations acting as outlet openings to output the product, wherein the product is configured to circulate through the at least one distribution cavity to and through the perforations for application to the skin by the application surface.

13. A device for applying a product to be distributed on the skin of a user by iontophoresis comprising:
- at least one storage container for storing the product to be distributed;
- at least one distribution cavity able to receive, from the at least one storage container, the product to be distributed;
- a distribution circuit containing distribution channels for distributing the product from the at least one storage container to the at least one distribution cavity;
- an application surface configured for direct contact with the skin of the user for applying the product on the skin;
- at least one first electrode for iontophoresis;
- an electronic control circuit;
- a measuring system, for measuring a physical or physicochemical parameter, connected to the electronic control circuit and configured to send a signal indicating the parameter measurement,
- wherein the at least one first electrode for iontophoresis and the measuring system are installed in the at least one distribution cavity, the electronic control circuit being configured to compare a measured value of the physical or physicochemical parameter in the at least one distribution cavity with a threshold reference value so as to detect an absence of product in the at least one distribution cavity, and wherein the at least one first electrode is set back from the application surface so that the at least one first electrode is spaced away from the skin of the user when the application surface is placed in direct contact therewith.

14. A device for applying a product to be distributed on the skin of a user by iontophoresis comprising:
- at least one storage container for storing the product to be distributed;
- at least one distribution cavity able to receive, from the at least one storage container, the product to be distributed;
- an application surface configured for direct contact with the skin of the user for applying the product on the skin;
- at least one first electrode for iontophoresis;
- an electronic control circuit;
- a measuring system, for measuring a physical or physicochemical parameter, connected to the electronic control circuit and configured to send a signal indicating the parameter measurement,
- wherein the at least one first electrode for iontophoresis and the measuring system are installed in the at least one distribution cavity, the electronic control circuit being configured to compare a measured value of the physical or physicochemical parameter in the at least one distribution cavity with a threshold reference value so as to detect an absence of product in the at least one distribution cavity, wherein the at least one first electrode is set back from the application surface so that the at least one first electrode is spaced away from the skin of the user when the application surface is placed in direct contact therewith, and
- wherein the at least one distribution cavity is defined by a bottom wall having at least one distribution opening therein that outputs the product from the at least one storage container and into the at least one distribution cavity, and wherein the at least one first electrode and the bottom wall are both spaced relatively away from the application surface.

* * * * *